US00PP20848P2

(12) United States Plant Patent
Zary

(10) Patent No.: US PP20,848 P2
(45) Date of Patent: Mar. 16, 2010

(54) FLORIBUNDA ROSE PLANT NAMED 'JACBOUPU'

(50) Latin Name: *Rosa hybrida*
Varietal Denomination: JACboupu

(75) Inventor: Keith W. Zary, Thousand Oaks, CA (US)

(73) Assignee: Jackson & Perkins Wholesale, Inc., Hodges, SC (US)

( * ) Notice: Subject to any disclaimer, the term of this patent is extended or adjusted under 35 U.S.C. 154(b) by 40 days.

(21) Appl. No.: 12/215,678

(22) Filed: Jun. 27, 2008

(51) Int. Cl.
*A01H 5/00* (2006.01)

(52) U.S. Cl. ..... Plt./148

(58) Field of Classification Search ..... Plt./148
See application file for complete search history.

(56) References Cited

U.S. PATENT DOCUMENTS

PP10,282 P * 3/1998 Zary ..... Plt./143
PP12,128 P2 * 10/2001 Zary ..... Plt./142
PP16,705 P2 * 6/2006 Zary ..... Plt./102

* cited by examiner

*Primary Examiner*—Wendy C Haas
(74) *Attorney, Agent, or Firm*—klarquist Sparkman, LLP

(57) ABSTRACT

A new and distinct variety of floribunda rose plant characterized particularly by its compact rounded plant; bright pink flowers with a light cream petal reverse; "handpainted" upper petal surface; glossy dark green foliage which is resistant to rust and powdery mildew; and easily propagates and grows vigorously on its own root.

1 Drawing Sheet

Genus and species: *Rosa hybrida.*
Variety denomination: 'JACboupu'.

ORIGIN OF THE INVENTION

The present invention relates to a new and distinct variety of a Floribunda rose plant named 'JACboupu' which was originated by me by crossing the variety 'JACzotta', U.S. Plant Pat. No. 12,128 (the seed parent), with the variety 'JACment', U.S. Plant Pat. No. 10,282 (the pollen parent).

BACKGROUND OF THE INVENTION

The primary objective of this breeding was to produce a new floribunda rose variety having the qualities of a compact rounded plant with disease resistant dark green foliage, brightly colored flowers, rapid repeat bloom and the ability to be propagated and grow vigorously on its own roots.

BRIEF SUMMARY OF THE INVENTION

The objective was substantially achieved, along with other desirable improvements, as evidenced by the following unique combination of characteristics, that are outstanding in the new variety, and that distinguish it from its parents, as well as from all other varieties of which I am aware:

1. A compact rounded plant.
2. Bright pink flowers with a light cream petal reverse.
3. The upper surface of the petals has "handpainting."
4. Foliage is dark green, glossy and resistant to rust and powdery mildew.
5. Propagates easily and grows vigorously on its own roots.

Asexual reproduction of this new variety by cuttings, as performed at Wasco, Calif., shows that the foregoing and all other characteristics and distinctions come true to form and are established and transmitted through succeeding propagations.

COMPARISON WITH PARENTS

'JACzotta': 'JACboupo' is more compact, has smaller flowers, and has handpainting in the flowers. 'JACment': 'JACboupo' differs in flower color and petal count.

COMPARISON WITH SIMILAR VARIETY

'JAChanpa' (U.S. Plant Pat. No. 16,705) is similar in flower color to 'JACboupu' but much taller.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart © 2001, except where ordinary dictionary significance of color is indicated.

Parentage:

*Seed parent.*—'JACzotta' (PP12,128).
*Pollen parent.*—'JACment' (PP10,282).

FLOWER

Observations made from plants that were about 1.5 years of age at the start of the observations and were about four years old at the end of the observations and that were grown in a garden environment at Somis and Wasco, Calif.

Blooming habit: Continuous.

Bud:

*Size.*—About 3 to 3½ cm long and 1½ to 2 cm in diameter when the petals start to unfurl.

*Form.*—The bud form is blunt, topped.

*Color.*—When sepals first divide, bud color is White Group 155D with Yellow Group 8C at base. When half blown, the upper sides of the petals are, top ⅔: mainly Red Group 50A with venation of White Group 155D, bottom ⅓: White Group 155D with Yellow Group 8C at base; and the lower sides of the petals are White Group N155B with Yellow Group 8C at base.

*Sepals.*—Color: Upper surface: Yellow-Green Group 147D. Lower surface: Yellow-Green Group 144B. Length: 35–40 mm. Width: 8–10 mm. Shape: Subulate. Surface texture: Upper surface: Hoary. Lower surface: Glandular. There are three lightly appendaged sepals. There are two unappendaged sepals with glandular edges.

*Receptacle.*—Color: Yellow-Green Group 144B. Shape: Funnel. Size: Medium, about 6–8 mm long×6–8 mm wide. Surface: Smooth.

*Peduncle.*—Length: Short, averaging about 4–8 cm. Surface: Prickly, glandular. Color: Yellow-Green Group 144C. Strength: Stiff, erect.

Bloom:

*Size.*—Medium. Average open diameter is about 7–9 cm.

*Borne.*—Clusters of 5–9 blooms having pyramidal shape.

*Stems.*—Strength: Strong. Average length is about 30–40 mm with a diameter of 4–8 mm.

*Form.*—When first open: Bloom is cupped high centered. Permanence: Outer petals quill.

*Petalage.*—Number of petals under normal conditions: 25–35.

*Color.*—The upper sides of the petals are, top ⅔: mainly Red Group 50A with venation of White Group 155D; bottom ⅓: White Group 155D with Yellow Group 8C at base. The reverse sides of the petals are White Group N155B with Yellow Group 8C at base. The base of each petal is Yellow Group 8C. The major color on the upper side is Red Group 50A.

*Variegations.*—White Group 155D.

*Discoloration.*—The general tonality at the end of the first day: White Group N155B. At the end of the third day: Red Group 50A. Day 5 lightens to Red Group 54C.

*Fragrance.*—Slight with a spicy character.

Petals:

*Texture.*—Leathery.

*Shape.*—Obdeltoid.

*Surface.*—Smooth.

*Margin.*—Entire. Apex Shape: Cuspidate. Base Shape: Cuneate.

*Form.*—Moderately quilled, petals thick.

*Arrangement.*—Imbricated.

*Petaloids.*—Number: 4–8, 12–16 mm long×8–10 mm wide. Color: upper: Red Group 50A with venation of White Group 155D. lower: White Group N155B.

*Persistence.*—Petals drop off cleanly before drying.

*Lastingness.*—On the plant: Fair (about 5–6 days). As a cut flower: Fair (about 6 days).

Reproductive parts:

*Stamens.*—Number: 90–100. Length: 7 mm. Anthers: Length: 2 mm. Color: Yellow-Orange Group 16B. Arrangement: Regular around styles. Filaments: Color: Yellow-Orange Group 16D. Length: 5 mm Pollen: Color: Greyed-Orange Group N167B.

*Pistils.*—Number: 35. Length: 6 mm. Styles: Color: Yellow-Green Group 1C. Length: 5 mm. Stigmas: Color: Yellow-White Group 158C. Length: 1 mm.

*Hips.*—Color: None observed.

PLANT

*Form.*—Bush.

*Growth.*—Vigorous, branching, compact.

*Age to maturity.*—2 years.

*Mature plant.*—Height: About 3 to 3.5 feet (90–100 cm). Width: About 3 feet (90 cm).

*Rootstock.*—Own root.

Foliage: Number of leaflets on normal mid-stem leaves: 5.

*Size.*—Medium, about 100 mm long×75 mm wide.

*Quantity.*—Abundant.

*Color.*—New foliage: Upper side: Greyed-Purple Group N186C quickly turning green. Lower side: Greyed-Red Group 178A quickly becoming green. Old foliage: Upper side: Green Group 139A. Lower side: Yellow-Green Group 147C.

Leaflets:

*Size.*—About 35 mm long×28 mm wide.

*Shape.*—Pointed oval.

*Base shape.*—Rounded.

*Apex shape.*—Acuminate.

*Texture.*—Leathery.

*Edge.*—Serrated.

*Serrations.*—Single.

*Petiole.*—Color: Green Group 137D.

*Petiole rachis.*—Color: Greyed-Purple Group 183B. Underside: Rough with prickles.

*Auricle shape, if present.*—Ensiform.

*Stipules.*—Length: 25 mm, serrated.

*Disease resistance.*—Susceptible to blackspot; mildew and rust resistant under normal growing conditions.

*Pest resistance.*—None observed.

*Vein color.*—Green Group 139A.

*Venation pattern.*—Reticulate.

Wood:

*New wood.*—Color: Yellow-Green Group 146C. Bark: Smooth.

*Old wood.*—Color: Yellow-Green Group 146B. Bark: Smooth.

Prickles:

*Quantity.*—On main canes from base: Ordinary. On laterals from main canes: Ordinary.

*Form.*—Straight.

*Length.*—6–7 mm.

*Color when young.*—Yellow-Green Group 146C.

*Color when mature.*—Greyed-Orange Group 177A.

Small prickles:

*Quantity.*—On main stalks: None. On laterals: None.

Winter hardiness: Hardy to Zone 5.

I claim:

1. A new and distinct variety of floribunda rose plant, substantially as herein shown and described, characterized particularly by its compact rounded plant; bright pink flowers with a light cream petal reverse; "handpainted" upper petal surface; glossy dark green foliage which is resistant to rust and powdery mildew; and easily propagates and grows vigorously on its own root.

* * * * *

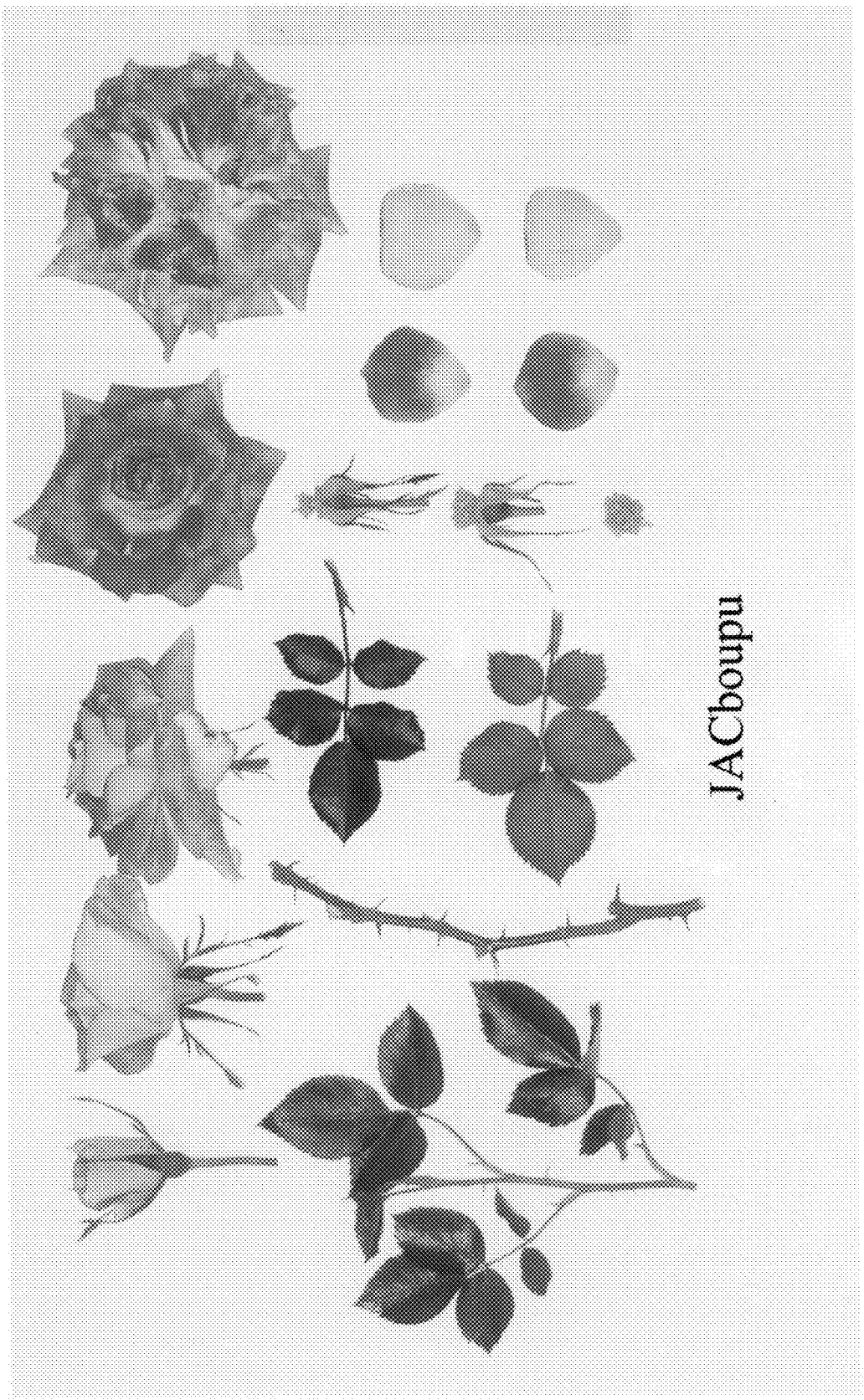
JACboupu